US00PP09220P

United States Patent [19]

van der Knaap

[11] Patent Number: Plant 9,220

[45] Date of Patent: Jul. 25, 1995

[54] DIEFFENBACHIA PLANT 'MAROBA' CULTIVAR

[76] Inventor: Eduard J. M. van der Knaap, Wilgenlei 15, 2665 KN Bleiswijk, Netherlands

[21] Appl. No.: 258,994

[22] Filed: Jun. 13, 1994

[51] Int. Cl.[6] ..... A01H 5/00

[52] U.S. Cl. ..... Plt./88.2

[58] Field of Search ..... Plt. 88.2

[56] References Cited

U.S. PATENT DOCUMENTS

P.P. 2,869 2/1969 Chaplin ..... Plt./88.2

P.P. 5,879 2/1987 Hollevoet ..... Plt./88.2

*Primary Examiner*—James R. Feyrer

*Attorney, Agent, or Firm*—Burns, Doane, Swecker & Mathis

[57] ABSTRACT

The new cultivar of *Dieffenbachia amoena* originated as a mutation of the Tropic Snow cultivar U.S. Plant. Pat. No. 2,869). The new cultivar can be readily distinguished from its parent cultivar by the exhibition of a compact erect growth habit and a greater quantity of irregular greenish-yellow markings on the leaves. The leaf blades of the new cultivar tend to be more coriaceous and more undulated, and the upper surface of the leaves is more glossy. Additionally, the lower leaves of the new cultivar tend to remain fresh considerably longer and tend to be retained on the plant substantially longer than those of the parent cultivar. A highly attractive foliage plant is provided for use as an ornamental house plant.

1 Drawing Sheet

SUMMARY OF THE INVENTION

The new and distinct cultivar of *Dieffenbachia amoena* was discovered during January, 1988 in my nursery at Bleiswijk, The Netherlands, while growing among plants of the Tropic Snow cultivar (U.S. Plant Pat. No. 2,869). The new variety is considered to be a spontaneous mutation of unknown causation. Had I not discovered and preserved the new cultivar it would have been lost to mankind.

It was found that the new cultivar of the present invention:

(a) exhibits an erect and compact growth habit,
(b) exhibits a greater quantity of irregular greenish-yellow markings on the leaves than the Tropic Snow cultivar,
(c) exhibits leaves that are more coriaceous and more undulated than the Tropic Snow cultivar,
(d) exhibits leaves that are more glossy on the upper surface than the Tropic Snow cultivar, and
(e) tends to retain lower leaves longer in a fresh condition than the Tropic Snow cultivar.

The new cultivar is particularly suited for growing as attractive ornamentation as a house plant.

Asexual reproduction by cuttings performed at Bleiswijk, The Netherlands, has demonstrated that the characteristics of the new cultivar as disclosed herein are firmly fixed and are retained through successive generations of asexual propagation.

When the new cultivar is compared to the Tropic Sun cultivar (U.S. Plant Pat. No. 5,879), the sibling Tropic Sun cultivar is seen to exhibit broader leaves, a more compact growth habit, and more greenish-yellow variegation on the leaves.

Also, when compared to the Tropic Sun cultivar, the new cultivar commonly exhibits darker green petioles and petiole sheaths, distinctly more undulations of the leaf margins, more dark green elongated spots between primary lateral veins of mature leaves, more glossiness on the upper surfaces of the leaves that is particularly apparent on younger leaves, and a greater tendency to form suckers.

The new cultivar has been named the Maroba cultivar.

BRIEF DESCRIPTION OF THE PHOTOGRAPHS

The accompanying photographs show as nearly as true as it is reasonably possible to make the same in color illustrations of this character, typical specimens of an overall plant and leaf of the new cultivar. The illustrated plant was grown in a greenhouse at Bleiswijk, The Netherlands, while growing on its own roots and was reproduced from a cutting. The day temperature of the greenhouse was maintained at approximately 22° C. and the night temperature was maintained at approximately 20° C. when growing the illustrated plant.

FIG. 1 illustrates a single plant of the new cultivar with lateral shoots at an age of 13 months. Such plant is approximately 120 cm. in height and approximately 100 cm. in width. The highly compact growth habit of the new cultivar and the extensive greenish-yellow leaf markings are apparent.

FIG. 2 illustrates for comparative purposes the underside of a typical leaf of the new cultivar on the right, and the underside of a typical leaf of the parent Tropic Snow cultivar on the left. A substantially greater amount of greenish-yellow variegation is apparent on the leaf of the new cultivar.

DETAILED DESCRIPTION

Figure 1:
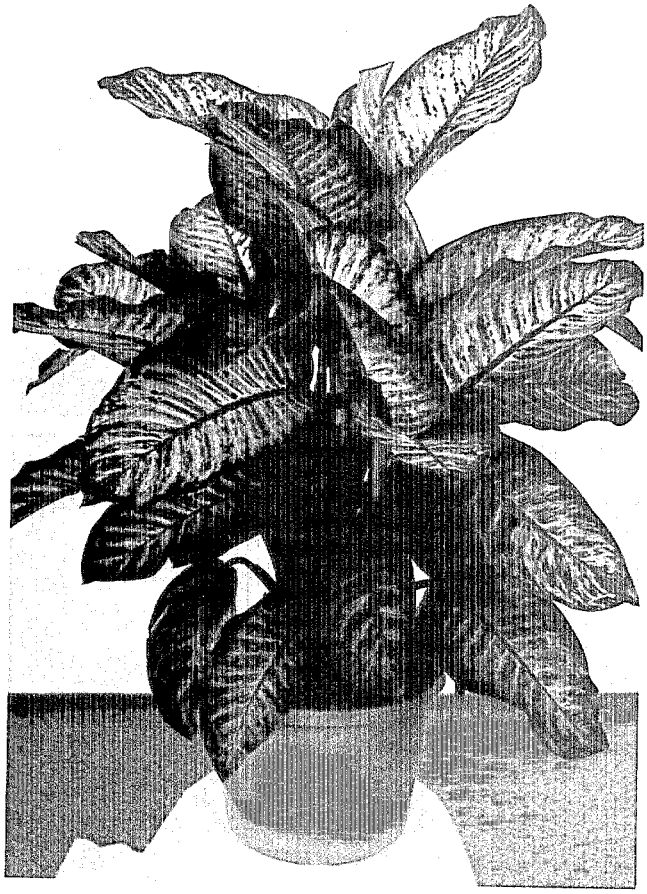
Figure 2:
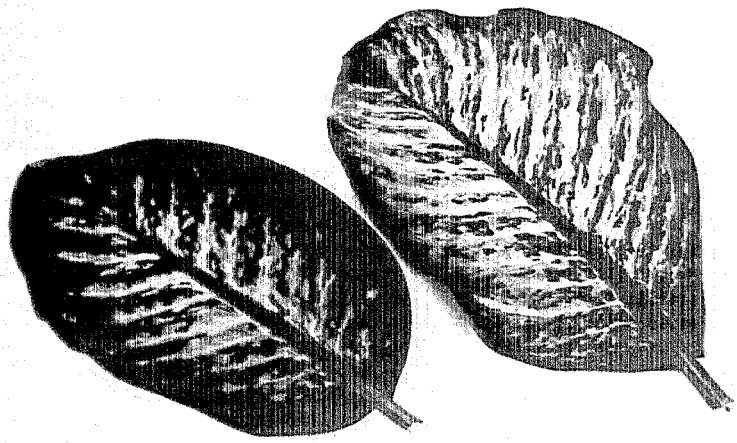

The following is a detailed description of my new cultivar with color terminology being used at some instances in accordance with The R.H.S. Colour Chart of The Royal Horticultural Society, London England. The description was made of plants reproduced by cuttings and growing in a greenhouse at Bleiswijk, The Netherlands.

Classification: *Dieffenbachia amoena,* cv. Maroba.

Plant:

*Growth habit.*—Slender, tall, erect, and quite compact.

*Height.*—After 38 weeks the plant commonly assumes a height of approximately 100 cm.

*Capacity of Suckering.*—Strong as exhibited by the parent Tropic Snow cultivar. The suckering habit of the new Maroba cultivar tends to be stronger than that of the sibling sport, Tropic Sun. For instance, a plant of the Maroba cultivar having a height of 70 cm. commonly exhibits 6 to 7 side shoots, while a plant of the Tropic Sun cultivar of the same height commonly exhibits only 3 to 4 side shoots under the same growing conditions. Also, as plants of the Maroba cultivar mature and assume a greater height approximately 7 to 8 side shoots commonly are observed.

*Flowering.*—The flowers are substantially identical to those produced by the parent Tropic Snow cultivar and erratically appear after the plant is approimately 38 weeks of age, and commonly appear after the plant is approximately 50 weeks of age.

*Foliage.*—Normal for type. Typical leaves of the new cultivar commonly have approximately the same length as those of the "Tropic Sun" cultivar; however, the maximum leaf widths for the new cultivar commonly measure approximately 20 to 22 cm., while those of the Tropic Sun cultivar commonly measure approximately 25 to 27 cm. The petiole and petiole sheath coloration commonly is darker than Green Group 139A for the new cultivar and Yellow-Green Group 147A for the Tropic Sun cultivar.

*Stability of color distribution during aging of leaf.*—There is a substantial quantity of irregular greenish-yellow variegation on the dark green leaves (as illustrated) that is particularly visible during the first 12 weeks. After the leaves achieve an age of approximately 12 weeks, there is a tendency for more green bands to form between the secondary veins.

Main stems:

*Internodes.*—Approximately 2 cm. on plants having a height of 70 to 100 cm.

*Diameter.*—Large, approximately 8 cm. on mature plants.

*Number of colors.*—One.

*Dominant color.*—Dark green.

Petiole:

*Length in relation to that of blade.*—Long, and approximately equal to the length of the blade.

*Number of colors.*—One.

*Dominant color.*—Dark green.

Leaf:

*Texture.*—Undulated with raised secondary veins.

*Size.*—Large, approximately 40 cm. in length.

*Shape.*—Elliptic-ovate with a cordate base.

*Width.*—Medium, approximately 22 cm.

*Shape of apex.*—Acute with distinct apiculum.

*Number of colors on upper side of main vein.*—One, dark green.

Leaf blade:

*Color distribution.*—Variegated (as illustrated).

*Type of variegation.*—The main vein and the leaf margins are dark green in coloration and commonly approach or are darker than Yellow-Green Group 147A, the side veins commonly approach Yellow Group 4D, and the bordering veins commonly are near Yellow Group 2B. The primary lateral veins commonly are white Group 155D in coloration. Between veins there are varying shades of yellowish-green that are irregularly disposed. More specifically, between the lateral veins commonly are formed irregularly shaped areas or spots of varying shades of green and white, including those that are darker than Green Group 139A, slightly paler than Yellow-Green Group 145A, Yellow-Green Group 144C, and those that are varying shades of grayish-green with no R.H.S. Colour Chart match. The irregular dark green variegation on the underside of the blade may be somewhat visible through the upper blade surface.

*General Appearance.*—Coriaceous and glossy on upper surfaces.

I claim:

1. The new and distinct cultivar of *Dieffenbachi,* substantially as herein shown and described, having the following combination of characteristics:

(a) exhibits an erect and compact growth habit,
(b) exhibits a greater quantity of irregular greenish-yellow markings on the leaves than the Tropic Snow cultivar,
(c) exhibits leaves that are more coriaceous and more undulated than the Tropic Snow cultivar,
(d) exhibits leaves that are more glossy on the upper surface than the Tropic Snow cultivar, and
(e) tends to retain lower leaves longer in a fresh condition than the Tropic Snow cultivar.

* * * * *